(12) United States Patent
Haga et al.

(10) Patent No.: US 8,680,483 B2
(45) Date of Patent: Mar. 25, 2014

(54) FLUORESCENCE DETECTOR

(75) Inventors: Takanobu Haga, Tachikawa (JP); Tsuyoshi Sonehara, Kokubunji (JP); Kenko Uchida, Tokyo (JP); Tomoyuki Sakai, Kokubunji (JP); Satoshi Takahashi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 238 days.

(21) Appl. No.: 13/141,127

(22) PCT Filed: Dec. 22, 2009

(86) PCT No.: PCT/JP2009/007097
§ 371 (c)(1),
(2), (4) Date: Jul. 28, 2011

(87) PCT Pub. No.: WO2010/073605
PCT Pub. Date: Jul. 1, 2010

(65) Prior Publication Data
US 2011/0272596 A1    Nov. 10, 2011

(30) Foreign Application Priority Data

Dec. 24, 2008    (JP) .................................. 2008-326793

(51) Int. Cl.
*G01J 1/58*    (2006.01)

(52) U.S. Cl.
USPC ..................................................... 250/458.1

(58) Field of Classification Search
USPC ............ 250/458.1, 459.1; 356/246, 317, 318; 385/12
See application file for complete search history.

(56) References Cited

U.S. PATENT DOCUMENTS

| | | | |
|---|---|---|---|
| 5,738,825 | A | 4/1998 | Rudigier et al. |
| 6,274,872 | B1 | 8/2001 | Katerkamp |
| 6,440,748 | B1 | 8/2002 | Katerkamp et al. |
| 2004/0155309 | A1 | 8/2004 | Sorin et al. |
| 2006/0170918 | A1 | 8/2006 | Nishiuma |
| 2008/0158570 | A1* | 7/2008 | Gollier et al. .................. 356/521 |
| 2009/0079978 | A1* | 3/2009 | Kimura ........................ 356/301 |

FOREIGN PATENT DOCUMENTS

| | | | |
|---|---|---|---|
| JP | 8-504955 | A | 5/1996 |
| JP | 10-090169 | A | 4/1998 |
| JP | 10-300667 | A | 11/1998 |
| JP | 10300667 | A  * | 11/1998 |
| JP | 11-190694 | A | 7/1999 |

(Continued)

OTHER PUBLICATIONS

T. Funatsu et al., Imaging of single fluorescent molecules and individual ATP turnovers by single myosin molecules in aqueous solution, Letters to Nature, vol. 374, Apr. 6, 1995, pp. 555-559.

(Continued)

*Primary Examiner* — Mark R Gaworecki
(74) *Attorney, Agent, or Firm* — Mattingly & Malur, PC

(57) ABSTRACT

A fluorescence detector in which a sample substrate is provided with a structure unit comprising a prism or a diffraction grating. After excitation light falling on the sample substrate is totally reflected at a biomolecule-immobilized face that is located in the opposite side of the structure unit, the structure unit allows the emission of the reflected light therefrom. To ensure multiple visual field measurement, a sample substrate-driving unit is provided to scan the sample substrate.

5 Claims, 15 Drawing Sheets

(56) References Cited

FOREIGN PATENT DOCUMENTS

| | | |
|---|---|---|
| JP | 11-304693 A | 11/1999 |
| JP | 2000-515966 A | 11/2000 |
| JP | 2001-521167 A | 11/2001 |
| JP | 2003-75337 A | 3/2003 |
| JP | 2003-121349 A | 4/2003 |
| JP | 2003-121350 A | 4/2003 |
| JP | 2003-202285 A | 7/2003 |
| JP | 2004-156911 A | 6/2004 |
| JP | 2006-208294 A | 8/2006 |
| JP | 2007-192841 A | 8/2007 |
| JP | 2008-298771 A | 12/2008 |
| WO | 2008/012703 A1 | 1/2008 |

OTHER PUBLICATIONS

I. Braslavsky et al., Sequence information can be obtained from single DNA molecules, PNAS, vol. 100, No. 7, Apr. 1, 2003, pp. 3960-3964.

H.-P. Lehr et al, Real-Time Detection of Nucleic Acid Interactions by Total Internal Reflection Fluorescence, Analytical Chemistry, vol. 75, No. 10, May 15, 2003, pp. 2414-2420.

\* cited by examiner

FIG. 4
(A) BEFORE MOVEMENT
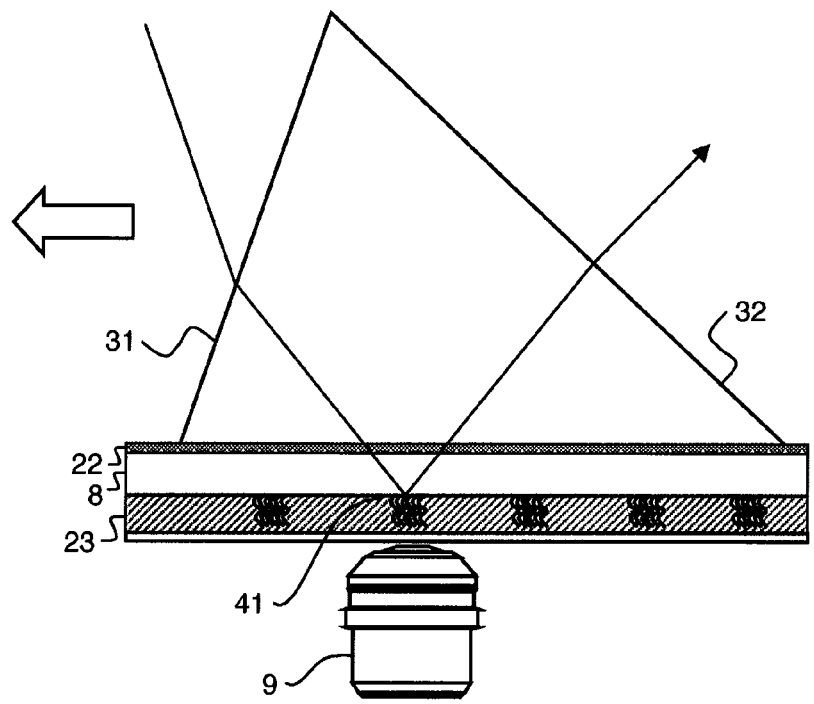
(B) AFTER MOVEMENT
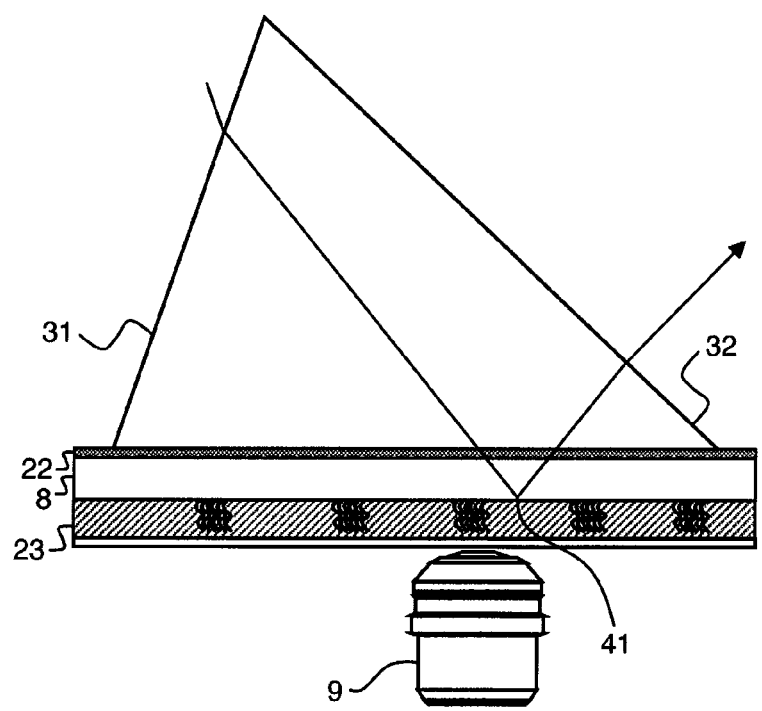

FIG. 8
(A) 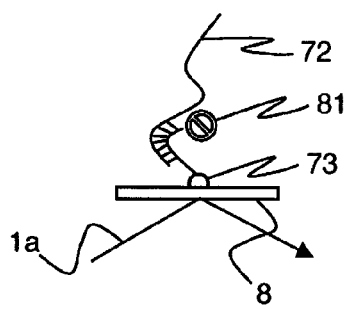
(B) 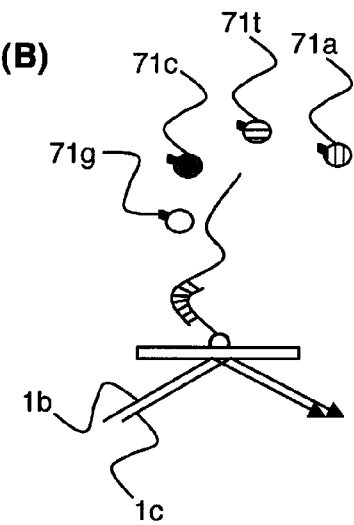
(C) 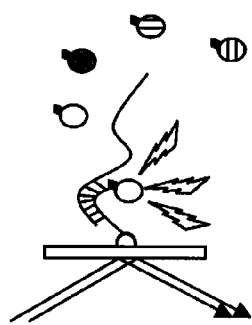
(D) 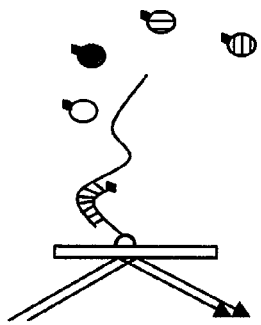
(E) 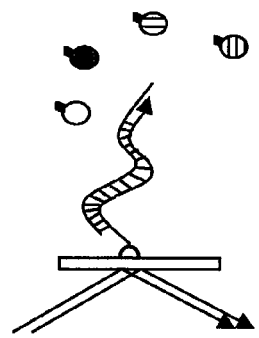

FLUORESCENCE DETECTOR

TECHNICAL FIELD

The present invention relates to an analysis technology for qualitatively detecting or quantifying a biomolecule by generating an evanescent field over the surface of a substrate of transparent material, exciting the fluorescently labeled biomolecule using this evanescent field, and detecting the resultant fluorescence which is emitted from the biomolecule as a result of the excitation. Here, the biomolecule is contained in a liquid sample provided on the substrate surface.

BACKGROUND ART

Conventionally, the single molecule fluorescence detection has been performed, which uses an evanescent field generated over the surface of a transparent sample substrate by illuminating the sample substrate with an excitation light output from an excitation light source and causing the excitation light to be totally-reflected inside the sample substrate.

For example, in Non Patent Literature 1, in order to generate an evanescent field in the single molecule fluorescence detection, a configuration is employed in which a flat face of a prism and the sample substrate are deployed in such a manner that they are in parallel and facing with each other and the spacing therebetween is filled with a matching solution to match the refractive indices of both of them.

Also, in Non Patent Literature 2, the monomolecular-level DNA sequencing is performed using the total-internal reflection illumination scheme. 532-nm-wavelength and 635-nm-wavelength lasers are utilized for the fluorescence detections of fluorophore Cy3 and fluorophore Cy5, respectively. Taking advantage of biotin-avidin protein binding, a single target DNA molecule is immobilized onto the sample substrate that is filled with the solution. Then, a primer, which is labeled with the one Cy3 molecule, is introduced into the solution by exchanging the solution so that its concentration becomes constant and a single fluorescently labeled primer molecule is hybridized with the target DNA molecule. At this time, the Cy3 exists in the evanescent field and the binding position of the target DNA molecule is confirmed based on the fluorescence detection. After the Cy3 is photobleached by irradiating the high-power 532-nm excitation light, thereby suppressing the fluorescence light emission thereinafter. Next, polymerase and a dNTP (N is any one of A, C, G, and T) equipped with one type of base, which is labeled with the one Cy5 molecule, are introduced into the solution by performing the solution exchange so that their concentrations become equal to constant values, respectively. As a result of this introduction, as long as the dNTP is in the complementary relationship with the target DNA molecule, a fluorescently labeled dNTP molecule is captured into the elongated strand of the primer molecule. At this time, the Cy5 molecule exists in the evanescent field and the complementary relationship can be confirmed based on the fluorescence detection at the binding position of the target DNA molecule. After the Cy5 is photobleach by irradiating the high-power 635-nm excitation light, thereby suppressing the fluorescence light emission thereinafter. The above-described dNTP-capturing reaction process is repeated sequentially in a step-wise manner with the type of the base such as, for example, A→C→G→T→A→ (step-wise elongation reaction) to determine a sequence of bases in the complementary relationship with the target DNA molecule. Also, a plurality of target DNA molecules are immobilized within a single field-of-view of a fluorescence-detected image and the above-described dNTP-capturing reaction process is processed in parallel so that the simultaneous DNA sequencing of the plurality of target DNA molecules can be implemented. It is expected that the number of the simultaneous parallel processings at this time can be made dramatically larger as compared with the case of the conventional capillary-electrophoresis-based DNA sequencing.

As a method of generating the evanescent field over the sample substrate, as described in Non Patent Literature 3, there also exists the following method. Namely, both ends of the sample substrate are machined to form oblique planes thereon and the laser light is introduced from the oblique plane formed. The laser light propagates by taking advantage of the multiple reflection inside the sample substrate and the sample-immobilized area is illuminated.

CITATION LIST

Non Patent Literature

Non Patent Literature 1: Funatsu et al., Nature Vol. 374, 555-559 (1995).
Non Patent Literature 2: Braslaysky et al., PNAS Vol. 100, 3960-3964 (2003).
Non Patent Literature 3: H. -P. Lehr et al., Anal. Chem. Vol. 75, 2414-2420 (2003).

SUMMARY OF INVENTION

Technical Problem

In the conventional single molecule fluorescence detection, when the sample substrate is deployed, it is required to fill the spacing between the prism and the sample substrate with a matching solution in order to prevent the air from intruding into the spacing. At this time, if air bubbles exist or if the air layer remains due to an insufficient amount of filling, the excitation light is scattered there to increase the background light or the optical path is altered so that the satisfying evanescent-illumination detection can not be executed. Meanwhile, if the matching solution is too much in amount, it turns out that the matching solution drops to make the apparatus dirty, for example, when the sample substrate is replaced. In this way, skill is needed when the matching solution is used.

Incidentally, as described in Non Patent Literature 3, the matching solution can be made unnecessary by, for example, forming oblique planes at both ends of the sample substrate. In this configuration, because the laser light is introduced from the oblique plane formed at the end of the sample substrate and subjected to multiple total reflection inside the sample substrate, a plurality of evanescent fields are generated. There exists a possibility that fluorescent molecules outside an observation field-of-view photobleach with the aforementioned evanescent fields and it becomes difficult to conduct the single molecule fluorescent measurement on a plurality of observation fields-of-view, thereby lowering the throughput. Accordingly, it is difficult to use this configuration to the DNA sequencer.

In this way, in the above-described conventional technology, no sufficient consideration has been given to a detector structure which is capable of providing excellent operability and is capable of forming the evanescent fields that allow implementation of the single molecule fluorescence detection on a plurality of observation fields-of-view.

Solution to Problem

A fluorescence detector of the present invention includes a light source, a detector deployed on a side of a first plane of a substrate including the first plane, on outer surface of which a plurality of biosamples are deployed, and a second plane, which a light from the light source enters and a light totally-reflected on outer surface of the first plane exits, for detecting a light emitted from one of the plurality of biosamples excited by an evanescent field generated on the outer surface of the first plane by the total reflection, and a driving unit for moving the substrate in such a manner that, of the plurality of biosamples, a second biosample is measured after a first biosample is measured.

Advantageous Effects of Invention

By providing a prism or diffraction-grating structure on the sample substrate an excitation light, which illuminates a sample-immobilized area inside an observation field-of-view with total reflection, can exit from the substrate through the structure without illuminating the sample areas outside the observation field-of-view. This feature makes it possible to prevent the fluorescent molecules outside the observation area from being photobleached and with driving the sample substrate execution of the observation of the plurality of fields-of-view becomes possible. Namely, an enhancement in the throughput is implemented.

BRIEF DESCRIPTION OF DRAWINGS

FIG. 4 (A) and FIG. 4 (B) illustrate an illumination shift at the time when perpendicularity of an incidence angle is broken in the first embodiment.

FIG. 8 (A)-FIG. 8 (E) illustrate a conceptual diagram of the real-time DNA-sequence determination method in the first embodiment.

DESCRIPTION OF EMBODIMENTS

Hereinafter, in accordance with the drawings, the explanation is given concerning embodiments of the present invention.

Embodiment 1

Figure 1:
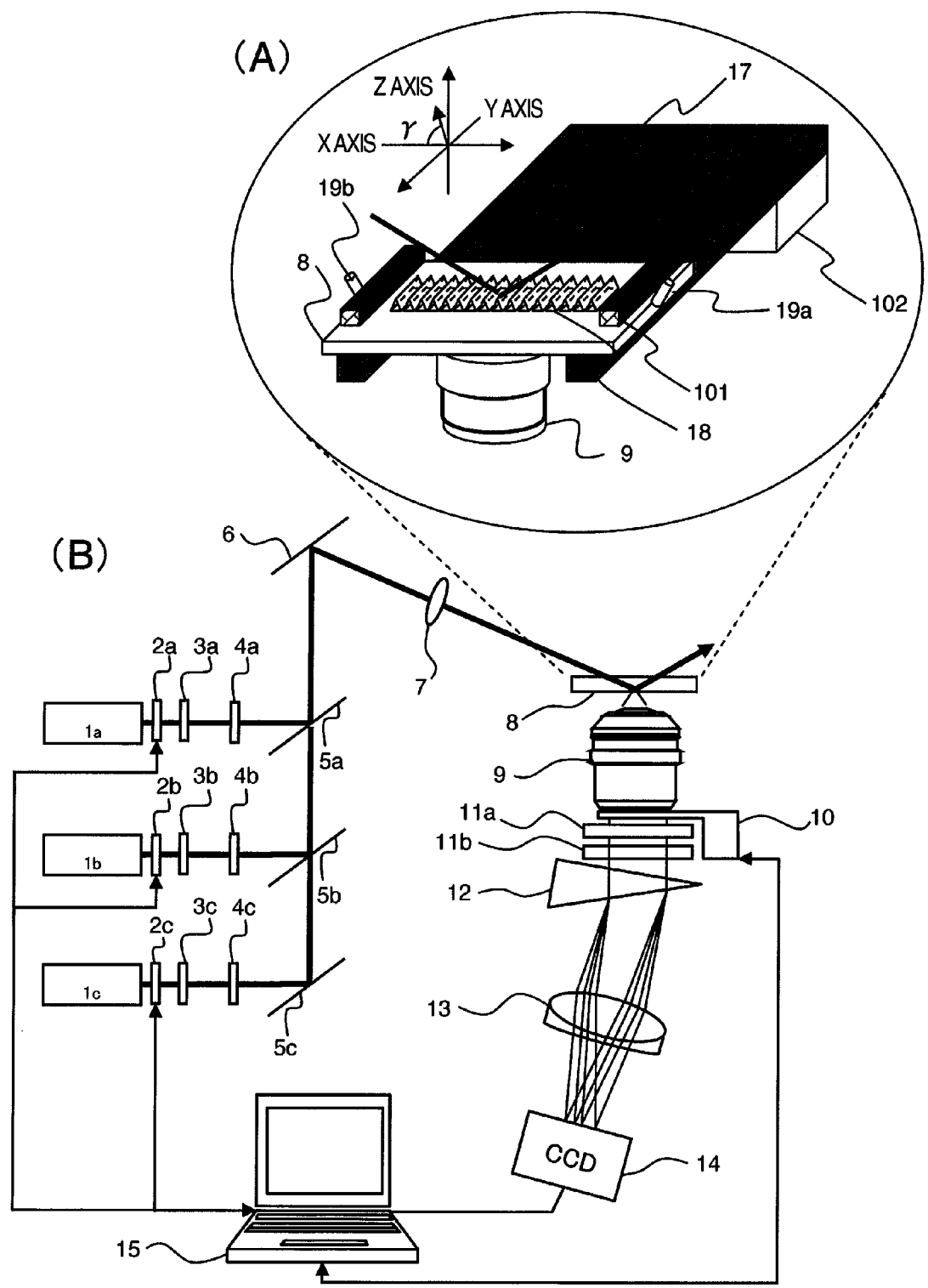
FIG. 1 illustrates configuration diagrams of a first embodiment of the present invention, where FIG. 1 (A) is an enlarged perspective view around a sample substrate and FIG. 1 (B) is a diagram of the entire configuration.
Figure 2:
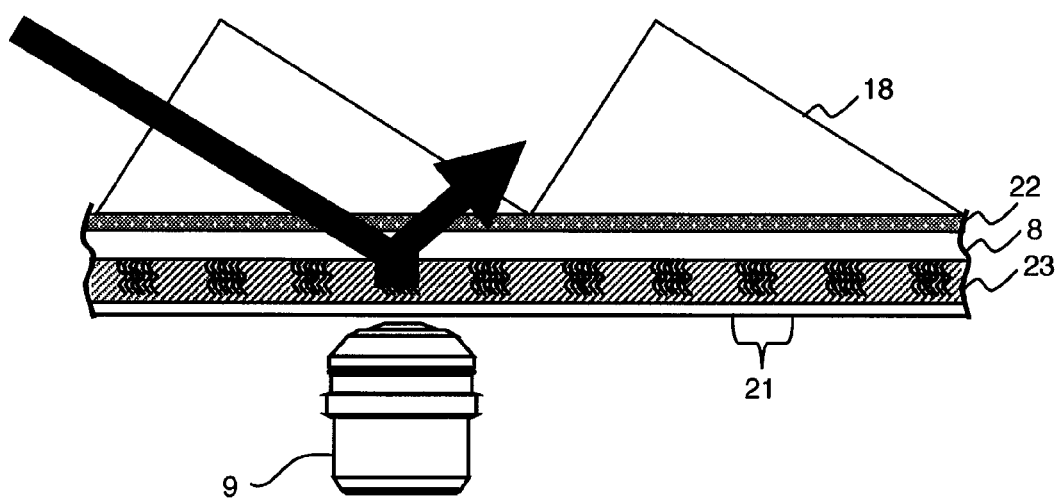
FIG. 2 illustrates a cross-sectional view including an excitation light path in the sample substrate in the first embodiment.

FIG. 1 illustrates configuration diagrams of a first embodiment of the present invention. The configuration of a sample substrate 8 and its periphery is illustrated in FIG. 1 (A) as its enlarged perspective view. The X, Y, and Z axes are defined as specified in FIG. 1 (A). A plurality of prism units 18 are provided on the sample substrate 8 and, as illustrated in FIG. 2, a plurality of sample areas 21 are provided on the opposite surface to a single prism unit 18. A sample area refers to an area onto which biomolecules (i.e., DNAs in the present embodiment) are immobilized. The sample area may also refer to an area which is observed using an objective lens 9 during scan. As illustrated in FIG. 2, forming the sample area in alignment with the field-of-view area observed by the objective lens 9 is preferable since it can detect all the immobilized biomolecules. The excitation light is made to enter the incidence plane of the prism with an angle which is substantially perpendicular thereto.

Sample-supporting members 101 in FIG. 1 (A) are set up for firmly fixing the sample substrate 8 by pressing it against a sample stage 17. This makes it possible to prevent an irregular position shift of the sample substrate 8 caused by its drift during the measurement.

In the present embodiment, two pieces of 2-mm-thick and 35-mm×5-mm polycarbonate plates are used as the sample-supporting members 101 and through holes are bored to put screws through at both ends of each polycarbonate plate. Using screw holes of the sample stage 17, they are fastened with the sample substrate 8 placed therebetween to hold the sample substrate 8 firmly. Otherwise, something like flat springs can be used as the sample-supporting members 101.

The sample substrate 8 is fixed onto a sample-driving unit 102 which is movable in the X, Y, and γ-axis directions. By controlling this unit 102 manually or automatically with a control unit 15, it becomes possible to scan the sample substrate 8 in the X and/or Y directions or to incline the sample substrate 8 by driving the γ axis. Here, γ is an angle which makes with the X axis within the X-Z plane. The γ axis can be used for correcting not only the inclination of the sample substrate 8 but also a shift of the total-reflection angle of the excitation light entering in parallel to the X-Z plane by inclining the incidence plane of the prism unit 18 by driving the γ axis. Since the intensity of the evanescent field formed on the sample-area side depends on the total-reflection angle, a variation in the fluorescence signal by the shift of the total-reflection angle can be suppressed. Also, in addition to the γ axis, the δ axis may be provided as the inclination-correcting measure for the sample substrate 8. Here, δ is an angle which makes with the Y axis within the Y-Z plane. The sample-driving unit 102 can add the Z axis further so that it can be used for such as the focus correction during fluorescence observation. The focus adjustment in the present embodiment is performed by driving the Z axis of an objective-lens driving unit 10 which supports the objective lens 9. At this time, the focus has been automatically adjusted using the control unit 15 while an image change in the sample-substrate surface detected by an image sensor 14 is fed back to the movement of the objective-lens driving unit 10.

Hereinafter, the explanation is given below concerning peripheral components of the optics system illustrated in FIG. 1. Monochromaticity of excitation lights emitted from excitation light sources 1a, 1b, and 1c are improved by excitation filters 3a, 3b, and 3c. After that, the excitation lights are converted into circularly polarized lights by λ/4 plates 4a, 4b, and 4c and reflected by dichroic mirrors 5a and 5b, or a mirror 5c, thereby being merged into one and the same light path. Moreover, the merged excitation light is reflected by an incidence-angle adjusting mirror 6, is focused by a condenser lens 7, enters the prism unit 18, and further enters the sample substrate 8. Then, the excitation light, which enters the sample substrate 8, is totally-reflected on an interface between the sample substrate 8 and a sample solution 23 to generate an evanescent field over the surface of the sample substrate 8 (FIG. 2). Light emission from the surface of the sample substrate 8 excited by the evanescent field is collected by the objective lens 9. Then, a component (i.e., elastically scattered light) of the light emission which has the same wavelength as that of the excitation light is eliminated by light-emission filters 11a and 11b. After that, the remaining light-emission is split into different directions on each wavelength basis by a dispersion prism 12 and imaged onto the image sensor 14 by a focusing lens 13. The image acquired by the image sensor 14 is recorded by the control unit 15, which has functions as a computer equipped with calculation, memory, and control functions.

In the present embodiment, a diode-excited solid laser of the wavelength of 355 nm, an Ar-ion laser of the wavelengths of 488 nm and 514.5 nm, and a laser diode of the wavelength of about 633 nm are used as the light source 1a, the light source 1b, and the light source 1c, respectively. Of course, others such as a Nd-YAG second-harmonics laser, a helium-neon laser, and a semiconductor laser may also be used. In the present embodiment, a fluorophore is used which has infrared, green, red, and orange light-emission wavelength bands whose spectra are separated. Since, in this case, the respective excitation wavelengths are different, the two light sources 1b and 1c are used as the excitation light sources corresponding thereto. For implementing simplicity of the fluorescence detector, a luminous body whose excitation wavelength band is broader as compared with that of the fluorophore, such as a quantum dot and a luminous body that uses a fluorescence resonance energy transfer (FRET), can be used as the method for making a light source single. In the former case, however, the particle size of the quantum dots and the luminous body that uses FRET is large, enzyme activity drops, and thus efficiency of the elongation reaction described later also lowers to increase the time needed for determination of the DNA sequence. Also, in the latter case, in addition to the problem of the particle size, detection efficiency of the fluorescence signal lowers and thus accuracy of the DNA-sequence determination also lowers if the FRET efficiency is low. Incidentally, while the light source 1a is used for implementation of the deprotection for starting the elongation reaction, it needs not be used in the case of a different reaction system. The illumination timings for the above-described light sources are implemented by opening/closing shutters 2a to 2c in accordance with a measurement method described later. The above-described operation is automatically controlled by the control unit 15. While a long-pass filter of transmitting for the wavelength of 525 nm or longer is used as the light-emission filter 11a and a notch filter for blocking the wavelength of 620 nm to 645 nm is used as the light-emission filter 11b, they may be, of course, band-pass filters for transmitting a wavelength range to be detected. A wedge prism made of BK7 material is used as the dispersion prism 12. It is desirable, however, to be a prism which exhibits less absorption and self-fluorescence in the light-emission wavelength range of a dye to be used. Also, it is possible to use a diffraction grating instead of the prisms.

Figure 3:
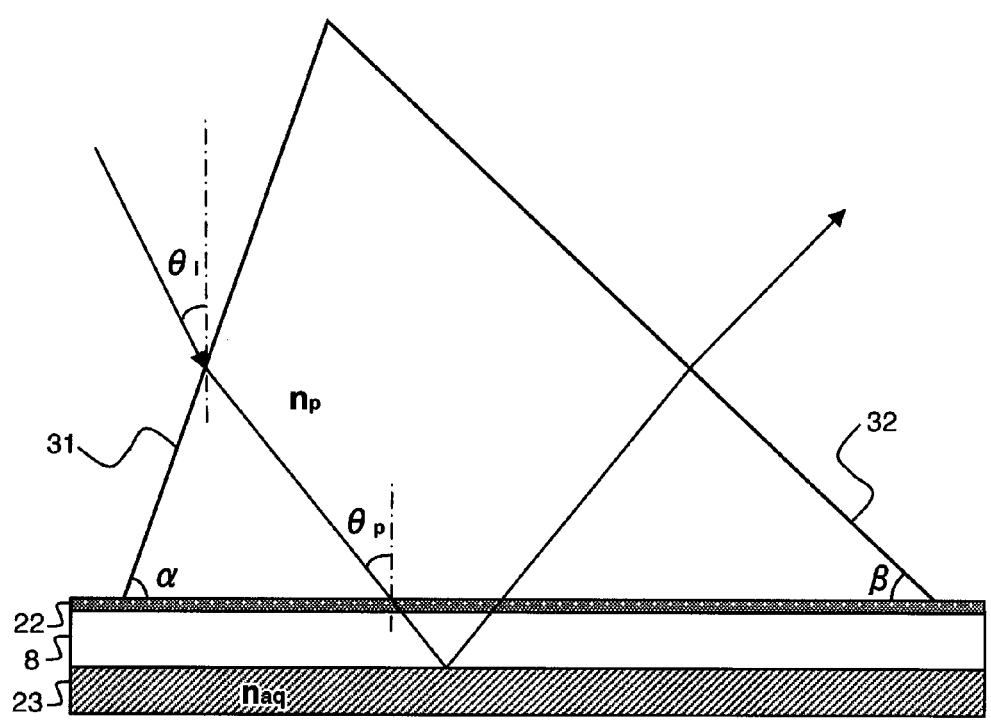
FIG. 3 illustrates the explanation of angles and refractive indices in the first embodiment.

Next, the explanation is given below concerning the profile of the prism unit 18 most suitable for the present invention. FIG. 3 illustrates a cross-section of the prism unit 18 and the sample substrate 8 including the excitation light path. $\theta_i$ is an incidence angle of the excitation light into the prism-unit incidence plane 31 with respect to the axis perpendicular to the sample substrate 8, α is an angle formed between the sample substrate 8 and the incidence plane 31, $\theta_p$ is an incidence angle from the prism unit 18 into an adhesive layer 22, and $n_p$ and $n_{aq}$ are refractive indices of the prism unit 18 and the sample solution 23, respectively. The conditions for the excitation light to be totally-reflected on the sample-substrate surface on the sample-area side are as follows:

$$\theta_p > \sin^{-1}(n_{aq}/n_p) \quad \text{(Equation 1)}$$

$$\sin(\theta_i - \alpha) = n_p \sin(\theta_p - \alpha) \text{ when } \alpha \leq \theta_p \quad \text{(Equation 2)}$$

$$\sin(\alpha - \theta_i) = n_p \sin(\alpha - \theta_p) \text{ when } \alpha > \theta_p \quad \text{(Equation 3)}.$$

Also, the condition on the angle β of a prism-unit exit plane 32 at which the totally-reflected excitation light exits to the outside the prism unit 18 is given by $$\beta > \theta_p - \sin^{-1}(1/n_p) \quad \text{(Equation 4)}.$$

In the present embodiment, with respect to a single prism unit 18, the plurality of sample areas 21 are provided in the X-axis direction and, accordingly, the incidence angle of the excitation light into the prism-unit incidence plane 31 is set at substantially 90°. This is because if the incidence angle is significantly out from perpendicular with respect to the incidence plane 31 as illustrated in FIG. 4, there is a possibility that the illumination area 41 shifts out from the observation field-of-view when the observation field-of-view is moved to the adjacent sample area 21 since the excitation light is refracted on the incidence plane 31.

Since $\alpha = \theta_p = \theta_i$ in the case of the normal incidence, the angle of the incidence plane is adjusted from Equation 1 so that $\alpha > \sin^{-1}(n_{aq}/n_p)$ is established. Concerning the angle formed between the prism-unit exit plane 32 and the sample substrate 8, it is desirable to hold $$\beta \approx 90° - \theta_p \quad \text{(Equation 5)}$$

so that no waste of illumination occurs and the sample areas 21 are more densely spaced.

The formation of the sample substrate 8 in the present embodiment is carried out by bonding 10-mm-high triangle-pillar prism units 18 (FIG. 1 (A)), each of which has a bottom face of a right triangle with α=60°, β=30°, and the three sides of 5-mm×10-mm×8.66-mm onto the quartz sample substrate of 18-mm×80-mm×1-mm (width×length×height) via the adhesive layer 22 with no spacing therebetween as illustrated in FIG. 1 (A). At this time, the material of each prism unit is S-BAL14 ($n_p$=1.57) and the refractive index of the sample solution 23 is $n_{aq}$=1.33. Accordingly, $\theta_p$>57.9° is established and the above-described profile of each prism unit 18 satisfies the conditions of (Equation 1) to (Equation 5). Incidentally, if the excitation light enters in the way that does not satisfy (Equation 1), the excitation light does not undergo the total reflection and transmits through the sample solution 23 so that the measurement sensitivity is lowered by increase of the background light caused by the water's Raman scattering. As a result the measurement accuracy of the single molecule fluorescence is lowered tremendously. PDMS is used as the adhesive layer 22 between the prism units 18 and the sample substrate. The bonding is performed so that the thickness between the prism units and the sample substrate becomes 0.1 mm or less while paying attention for air bubbles not intruding thereinto. It is desirable that the adhesive layer 22 be a one whose refractive index is similar to that of the prism units 18; however, it may be an refractive index which does not cause the total reflection on the interface between the prism units 18 and the adhesive layer 22 and a material which exhibits less absorption and self-fluorescence with respect to the excitation wavelength is preferably used. In addition to the above-described method, the sample substrate 8 can also be formed without using the adhesive layer by, for example, cutting the sufficiently-thick sample substrate 8 down to form the prism units or pouring a resin into a mold. Not limited to S-BAL14, the material of the prism units 18 and the sample substrate 8 may also be an arbitrary glass such as Bak4 or quarts, and further, even a resin. Namely, material which exhibits less absorption and self-fluorescence with respect to the excitation wavelength is desirable.

Figure 5:
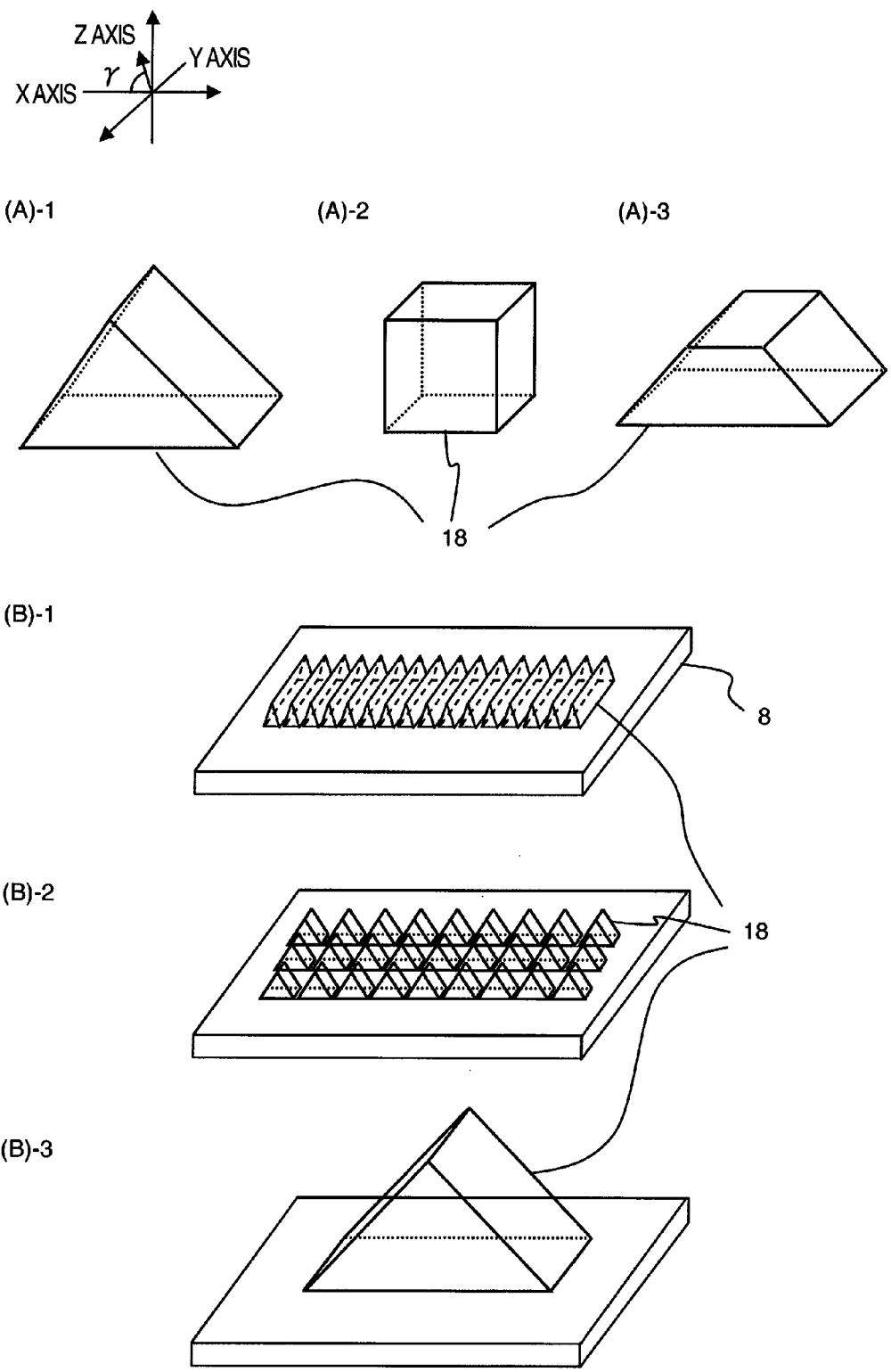
FIG. 5 (A) illustrates forms of variations of a prism unit in the first embodiment and FIG. 5 (B) illustrates deployment methods for the prism unit in the first embodiment.

In addition to the triangle pillar used in the present embodiment (FIG. 5 (A)-1), the profile of each prism unit 18 may also be a rectangular pillar whose bottom face is a rectangle (FIG. 5 (A)-2) or a trapezoid (FIG. 5 (A)-3). Also, the arrangement method for the prism units relative to the sample substrate 8 may be one like the present embodiment in which the prisms elongated in the Y-axis direction are arranged in a one-dimensional manner (FIG. 5 (B)-1) or another in which prisms smaller than these ones may be arranged in a two-dimensional manner (FIG. 5 (B)-2). Also, if the number of the plurality of sample areas 21 is small, the prism units 18 can be integrated and formed into a single prism unit ultimately as in FIG. 5 (B)-3. In this case, the angle $\beta$ is not needed to satisfy (Equation 5). However, if the number of the plurality of sample areas 21 is large and the scan distance of the sample substrate 8 becomes longer, the illumination-position shift illustrated in FIG. 4 becomes conspicuous along with the increase in the scan distance and strictness is required for the adjustment of the incidence angle.

Next, the explanation is given below concerning the components other than the prism units 18, which are illustrated in FIG. 1.

Figure 6:
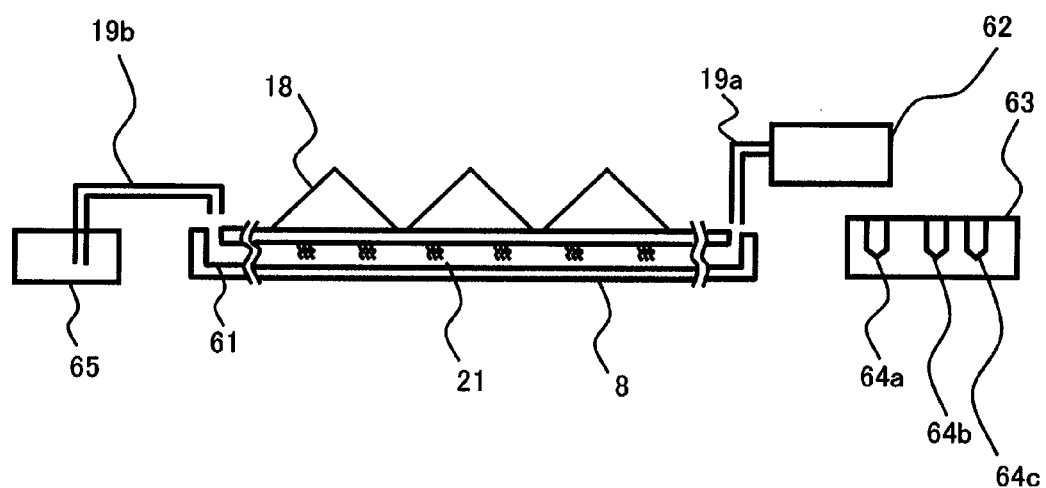
FIG. 6 illustrates a configuration diagram of a solution-conveying mechanism into a flow channel in the first embodiment.

As illustrated in FIG. 6, a flow channel 61 is formed on the sample substrate 8. This is carried out by attaching to a 18 mm×80 mm×1 mm quarts glass a same-sized PDMS substrate in which the flow channel 61 is engraved. A mechanism for execution of the solution exchange is implemented by flowing a target solution into an observation field-of-view in the sample substrate 8 via a flow-in channel 19*a* and a flow-out channel 19*b*, which are connected to both ends of the PDMS substrate. With the automatic control the solution exchange is carried out by connecting a solution-conveying unit 62 to target-solution reservoirs (sample reservoir 64*a*, buffer reservoir 64*b*, and reaction-solution reservoir 64*c*) contained in a solution-storing unit 63. The waste solution is stored into a waste-solution tank 65 via the flow-out channel 19*b*. The solution-storing unit 63 is equipped with a temperature-adjusting function and is capable of storing the solution in the reservoirs without degrading their qualities even in the case of long-time measurement.

Figure 7:
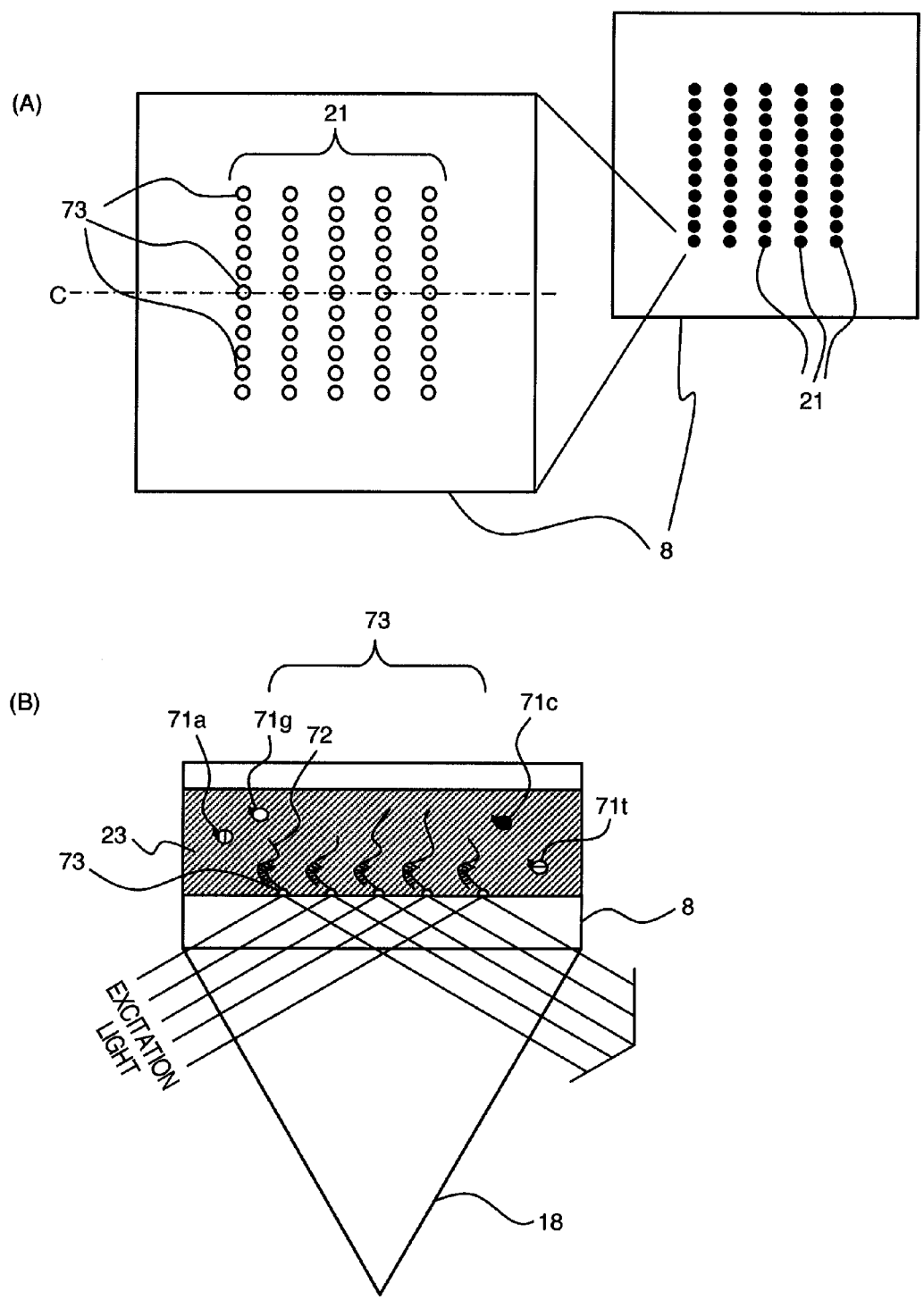
FIG. 7 (A) illustrates a front view around a sample area in the first embodiment and FIG. 7 (B) illustrates a cross-sectional view around the area along the dashed line C.

FIG. 7 illustrates enlarged views of the periphery of the sample areas 21 in the present embodiment. FIG. 7 (A) illustrates a front view and FIG. 7 (B) illustrates a cross-sectional view thereof along the dashed line C. The solution-conveying unit 62 is connected to the sample reservoir 64*a* in advance and the solution containing the double-stranded complexes 72 for which single-stranded target DNAs each of whose DNA-sequence is wished to be determined and a primer are hybridized is deployed, in the flow channel 61 so that the double-stranded complexes 72 are immobilized onto the surfaces of metal structures 73 whose material is gold. Since streptavidin is immobilized onto the surfaces of the metal structures, the double-stranded complexes can be immobilized by a specific interaction between the streptavidin and biotin at the 5' end of the primer. Besides the biotin, the employment of thiol also allows the double-stranded complexes to be specifically immobilized onto the gold surfaces. The metal structures 73 are controlled into a 50-nm-or-less size. The size of this order permits mutual electrostatic repulsion and steric hindrance between the double-stranded complexes 72 to exert sufficiently and a configuration is implemented where only a single molecule of the double-stranded complexes 72 is substantially bound to a single unit of the metal structures 73. The metal structures 73 are spaced in a 1-μm-pitch lattice-like manner by using semiconductor processes. Although in the present embodiment the EB lithography is used for the fabrication process, dry etching and/or wet etching may also be used. Also, the metal structures 73 are composed of gold, copper, aluminum, chromium, and the like, are of a profile having the size smaller than the wavelength of the excitation light, and are of a structure having rectangular, conical, cylindrical, and/or partially-protruding-portion-equipped structures.

In the present embodiment, the DNA sequence of target DNA is determined in real time using the configuration illustrated in FIG. 1 and based on reaction processes illustrated in FIG. 8. Here, a protecting group 81 which is bound to the 3' end of the primer of a double-stranded complex 72 for preventing the elongation reaction is removed by irradiating the light source 1*a* of the wavelength of 355 nm (deprotection) (FIG. 8A). The elongation reaction is started by deploying a reaction solution which contains fluorescently-labeled nucleotides 71*t*, 71*a*, 71*c*, and 71*g* and enzymes causing the elongation reaction under the irradiation of the light sources 1*b* and 1*c* (FIG. 8B). Here, the nucleotide 71*t* is thymine modified by the infrared-light-emitting fluorophore, the nucleotide 71*a* is adenine modified by the green-light-emitting fluorophore, the base 71*c* is cytosine modified by the red-light-emitting fluorophore, and the nucleotide 71*g* is guanine modified by the orange-light-emitting fluorophore. The sample substrate 8 is illuminated with the totally-reflected excitation light using the Ar-ion laser and the laser diode as the light sources 1*b* and 1*c*, respectively, and, every time one of the nucleotide is captured into the single-stranded DNA to elongate the complementary strand, the light emission corresponding to the elongated nucleotide is excited by the evanescent field (FIG. 8C) irradiates. Here, the fluorophores of the fluorescently-labeled nucleotides 71*a* and 71*g* are excited by the light source 1*b* and the fluorophores of the fluorescently-labeled nucleotides 71*t* and 71*c* are excited by the light source 1*c*. Light-bleaching or detaching the dyes eliminates the light-emission (FIG. 8D) and the next nucleotide is captured. Repeating the same process proceeds the elongation (FIG. 8E) and the difference in colors of the spots that emit light at that time results in the difference in spectrum profiles which enter the image sensor 15. Taking advantage of this the DNA sequence is determined. The object of the deprotection in the above-described process is to exert the control so that the elongation reaction does not start outside the observation field-of-view. Although in the present embodiment the allyl group is used as the protecting group 81, other functional groups may also be used.

Figure 9:
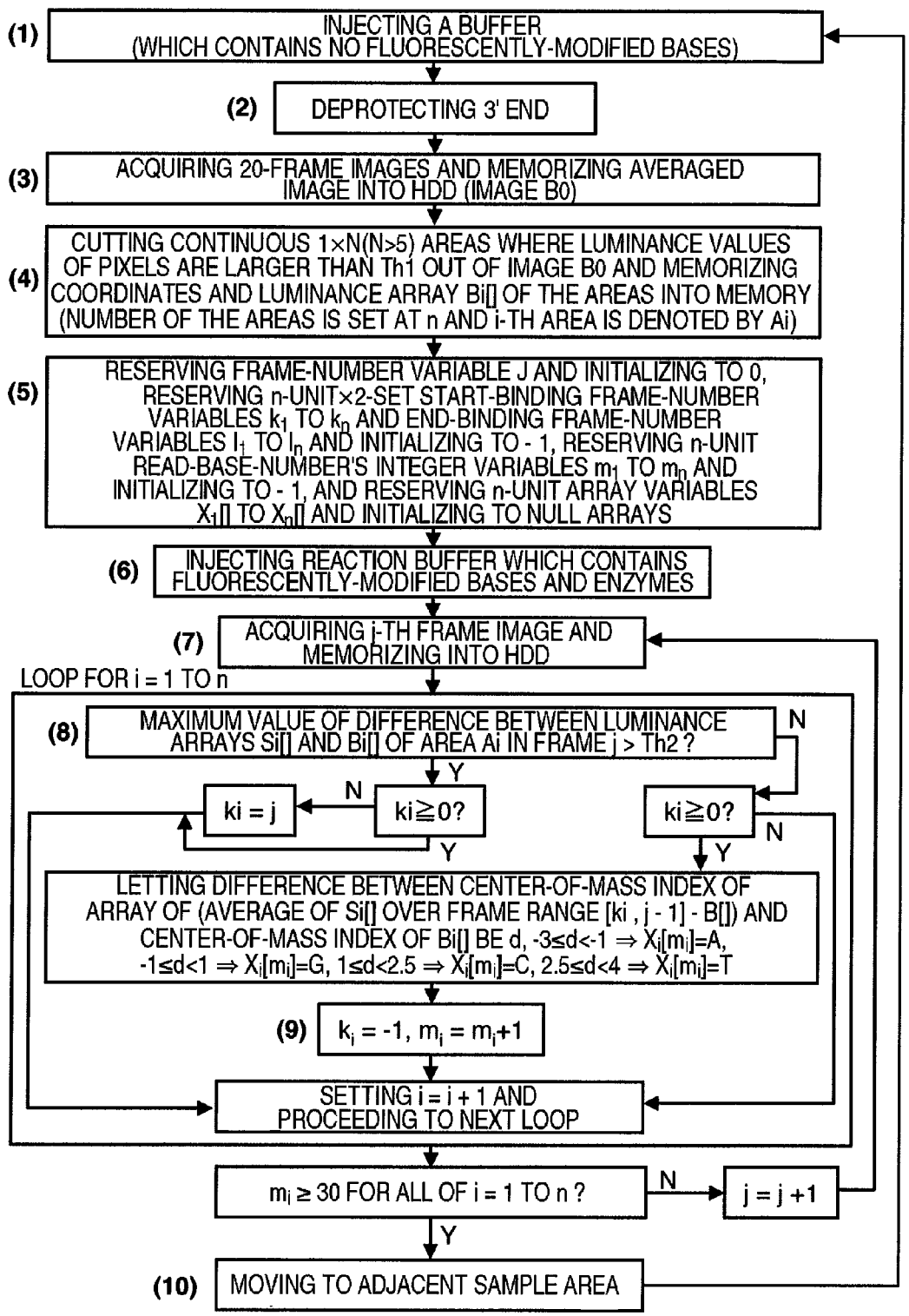
FIG. 9 illustrates a flowchart for the measurement steps in the first embodiment.

FIG. 9 illustrates a flowchart for indicating a detailed algorithm for judgment on the nucleotide type. Th1 and Th2 are a pre-determined threshold value for judging the light emission from the metal structure and a pre-determined threshold value for judging the light emission from biomolecules, respectively.

As a first step (1), the solution-conveying unit 62 is connected to the buffer reservoir 64b and a solution (a buffer) containing no fluorescently-labeled nucleotides or enzymes is injected into the flow channel 61 in the sample substrate 8 from the flow-in channel 19a. In this state, the light emission only from the gold-composed metal structure is observed. As a second step (2), the deprotection is performed by irradiating the light from the light source 1a in the observation field-of-view. As a third step (3), 20 frames of light-emission images only from this gold-composed metal structure 73 are acquired under the irradiation of the light source 1a, 1b, or 1c and averaged along the time axis. The light emission from the gold is not bleached and by averaging the large number of frames like these (that is, frames acquired during long-time measurement) it becomes possible to obtain an excellent S/N ratio even when light emission is weak. As a fourth step (4), areas in which the pixel values of N-or-more (N>2) continuous pixels in the spectral direction are larger than the threshold value Th1 are extracted out of the averaged image as light-emission spots of the gold. Since the summit angle of the prisms is set so that the light-emission wavelength (550 to 700 nm) of the gold is dispersed into 6 pixels in the present embodiment, N>5 is set. The number of the areas extracted here is made equal to n and the i-th area and a pixel array are denoted by Ai and Bi, respectively. Here, as a fifth step (5), variables used in a measurement loop (7) to (9) later are initialized. As a sixth step (6), the connection of the solution-conveying unit 62 is switched to the reaction-solution reservoir 64c and the reaction solution (the reaction buffer) which contains the fluorescently-labeled nucleotides and the enzymes is injected. From here the binding reactions of the bases onto the DNAs immobilized onto the gold nanometer-sized particles and the light emission of the modifying fluorophore start and the measurement loop (7) to (9) is repeated until an end of the measurement.

The variables initialized at (5) are used as follows. Frame-number variable j is the number of accumulated frames of images which are continuously acquired after the start of the measurement loop. A variable for memorizing the frame number at which the base is bound onto the i-th spot Ai and the light emission of the fluorophore is started is $k_i$. A variable for memorizing the frame number at which the fluorophore is removed from the base bound onto the spot and the light emission of the fluorophore is terminated is $l_i$. A variable for memorizing the number of times in which the binding/removal of the fluorophore into/from the spot Ai is repeated is $m_i$ (=1 to N). Namely, $m_i$ is the number of the bases read for the spot Ai. Also, n units of arrays $X_i$ for memorizing the DNA sequence read for each spot are reserved.

Every time a new frame j is acquired at Step (7), the following Step (8) is performed with respect to the n units of areas. Hereinafter, the explanation is given regarding the processing for the i-th area. First of all, if the difference between pixel array Si in the new frame of the area Ai and the already-recorded pixel array Bi for the light emission only from the gold exceeds the predetermined threshold value Th2, it is judged that a fluorophore, that is, a certain type of nucleotide, is bound onto the i-th spot. Then, if $k_i$<0, since no nucleotide is bound thereon at the previous frame, the new binding can be regarded as having occurred and the start-binding frame number $k_i$=j is set. If $k_i$≥0, since the fluorophore which is already bound thereon at the frame of j−1 or before merely continues to emit the fluorescence, i=i+1 is set without changing $k_i$ and the processing proceeds for the next spot. When the difference between Si and Bi is Th2 or less, it is judged that no fluorophore is bound and, if $k_i$<0, since no fluorophore is bound thereon already from the previous frame, i=i+1 is set and the processing proceeds for the next area. If $k_i$≥0, it is judged that the bound fluorophore is removed, the difference (this turns out to be the fluorescence spectrum of the fluorophore) between the average value of Si for the frames acquired from $k_i$ to j and Bi is calculated, the index is determined which is supposed to be the center-of-mass of this array, and the difference d from the center-of-mass index of Bi is determined. This d represents the central wavelength of the fluorescence spectrum of the fluorophore. Based on the fluorophore characteristics used in the present embodiment it is judged as the adenine-modifying fluorophore if −3≤d<−1, the guanine-modifying fluorophore if −1≤d<1, the cytosine-modifying fluorophore if 1≤d<2.5, and the thymine-modifying fluorophore if 2.5≤d<4. As Step (9), $k_i$=−1 and $m_i$=$m_i$+1 are set and the base corresponding to X[$m_i$] is memorized.

The above-described steps are executed on each frame basis for all of the spots and repeated until $m_i$≥30 for all of the spots. By this the sequence of 30-or-more bases is read for all of the spots. As Step (10), the field-of-view of the objective lens 9 is moved to the adjacent sample area by moving the sample substrate 8 using the sample-driving unit 102. After then, the above-described steps (1) to (10) are repeated, thereby scanning all of the sample areas.

In the present embodiment, the expression profiling of a messenger RNA is employed as its target application and, since it is effective enough to be able to decipher 30 bases, $m_i$≥30 is employed as the measurement end condition. For an application which necessitates a longer base length to be deciphered, for example, when deciphering the genome whose draft sequence is undetermined, the measurement end condition should be set to be a larger value such as, for example, $m_i$≥100 or $m_i$≥400. As described, with the configuration of the present embodiment, in addition to making the bad-operability matching solution unnecessary, measurement on the multiple fields-of-view is enabled by preventing the multiple total reflection in the sample substrate; as a consequence, the sample-processing capability can be improved.

Embodiment 2

The feature of a second embodiment is to make the spacing between the sample areas in the X-axis direction and the spacing between the prism units equal to each other.

In the first embodiment, the sample substrate is scanned to illuminate the plurality of sample areas with respect to one and the same prism-unit incidence plane for observation. In this case, the excitation light is required to enter the prism-unit incidence plane with normal incidence. If the excitation light deviates from this limitation, as illustrated in FIG. 4, the illumination area moves out from the observation field-of-view during scanning and measures such as optical-path correction are required. The larger the number of the sample areas which share one and the same prism unit in the X-axis direction becomes, the more conspicuous the above-described problem becomes.

Figure 10:
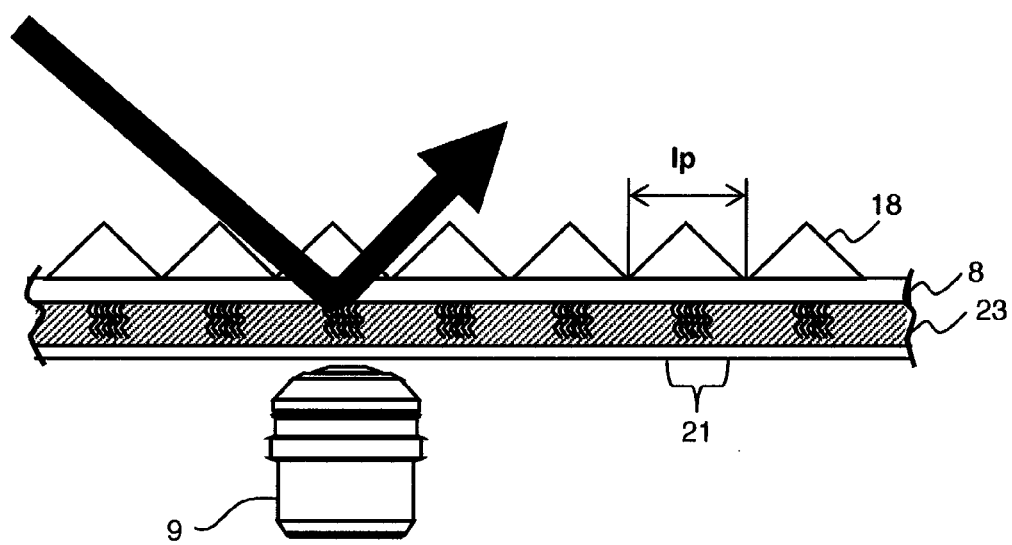
FIG. 10 illustrates a cross-sectional view including the excitation light path in the sample substrate in a second embodiment.

Therefore, in the present embodiment, as illustrated in FIG. 10, it is arranged that the spacing of the prism units 18 and the spacing of the sample areas 21 are equal to each other in the X-axis direction. The other configurations are the same as the ones illustrated in FIG. 1. The advantage in the above-described configuration is that the incidence position of the excitation light into the prism unit 18 remains unchanged so that the sample area 21 which is always deployed within the observation field-of-view can be illuminated even when the measurement field-of-view is moved to the next sample area by driving the sample substrate.

As for the profile of the prism unit, the angles of the oblique planes are required to satisfy the total-reflection conditions (Equation 1) to (Equation 3) and the exit condition (Equation 4). Further, it is desirable that (Equation 5) be satisfied in order to densely deploy the sample areas 21. In the present embodiment, the quarts sample substrate 8 is machined by etching into the profile of $\theta_p=66.8°$ as illustrated in FIG. 10 and $\alpha=60°$ and $\beta=25°$ are set. Then, by making the excitation light to enter with $\theta_i=70°$ with respect to the sample substrate 8, the right hand side of (Equation 1) is 65.6° since the refractive index of the quarts prism unit 18 is 1.46, which satisfies the condition. Also, the right hand side of (Equation 4) is 23.6° and this condition is also satisfied.

If the width of the prism is defined as lp illustrated in FIG. 10, by satisfying $$(\text{prism width } lp) \approx (\text{sample-area spacing}) \approx (\text{excitation-light irradiation area}) \geq (\text{observation field-of-view})$$

the sample areas can be deployed without waste. In the present embodiment, 60 fold as a magnification of the objective lens 9, 85 mm as a focal distance of the focusing lens 13, and 6.45-μm square as a pixel size of a 1344-pixel×1024-pixel CCD camera are used and the observation field-of-view becomes 233 μm×306 μm. Thus, the excitation-light illumination area on the sample substrate is set to 300 μm×840 μm (Y axis×X axis) by adjusting the focal distance and position of the condenser lens 7 and the prism units 18 and the sample areas 21 are formed so that the prism width lp=1000 μm and the sample-area spacing becomes equal to 1000 μm. Letting the length of the prism in the Y-axis direction be 10 mm, a single prism unit is to cover a plurality of sample areas 21. The profile is also allowable with which a single prism unit can cover only one sample-area field-of-view by letting it be 300 μm. The sample areas 21 is formed by arranging the metal structures 73 at a 1-μm spacing in 230-μm×300-μm (Y axis×X axis).

With the configuration of the present embodiment a shift of the illumination area by scanning is prevented and there is an advantage of reducing material cost by making the prism units smaller.

Embodiment 3

The refractive index of the prism varies depending on wavelength. When the excitation lights of the plurality of wavelengths enter the prism unit 18 with an angle off perpendicular like the second embodiment, in the incidence method as illustrated in FIG. 1 where the two light sources 1b and 1c are integrated into one and the same optical path, a shift from the same optical path occurs in the prism. Due to this, there is a possibility that the illumination position may shift by a degree of several hundreds of μm on the sample substrate 8 ultimately. The fine adjustment of the illumination-area position can be satisfactorily made by finely adjusting the position and the tilt of the condenser lens 7. In the above-described configuration, however, this adjustment method is not useful since the optical paths of the plurality of wavelengths move simultaneously. Then, it is conceivable to adjust the angle of the dichroic mirror 5b or 5c. However, if the optical-path length to the sample substrate is long, fine adjustment of a degree of several hundreds of μm is difficult.

Figure 11:
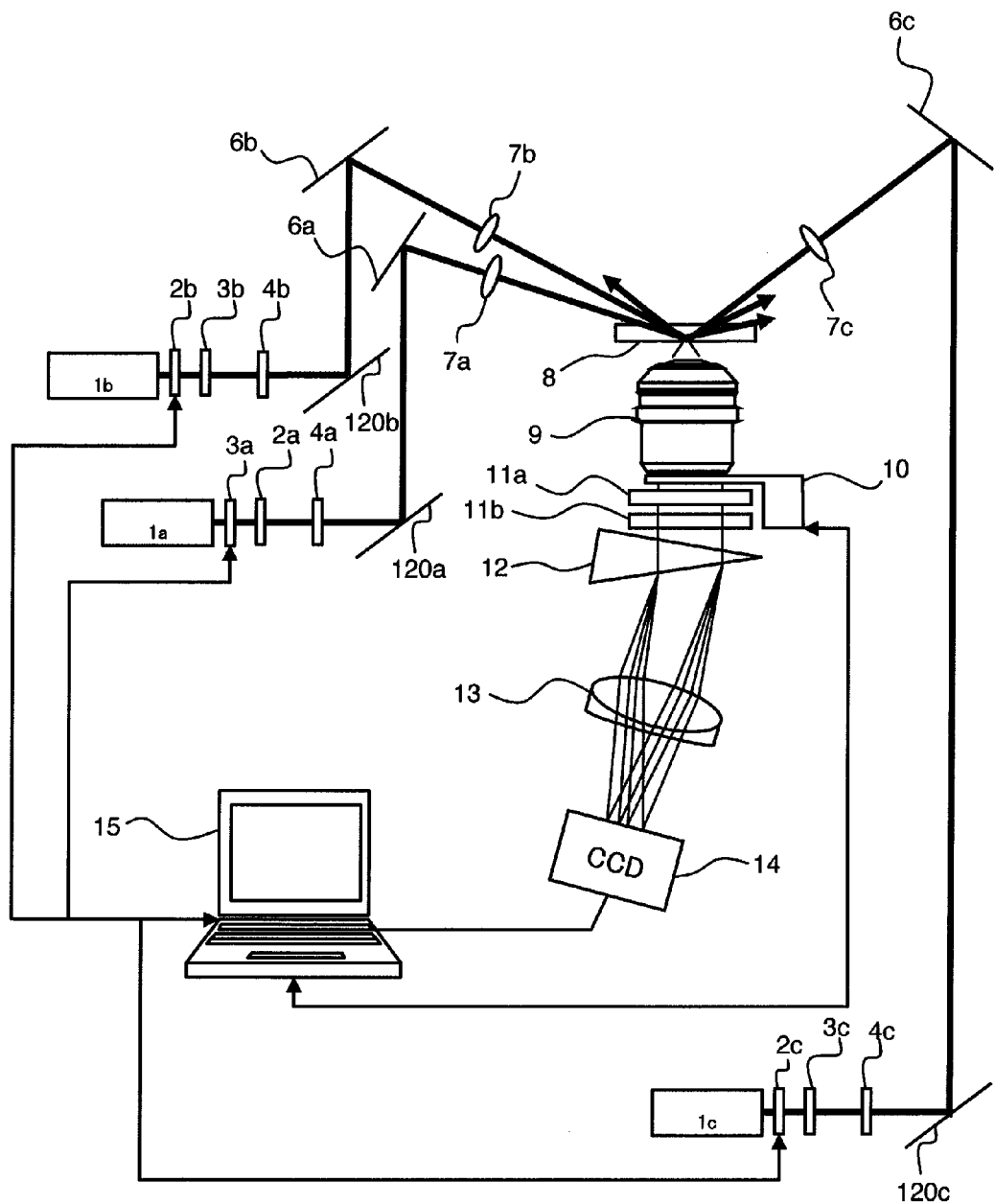
FIG. 11 illustrates a configuration diagram of a third embodiment.

As the method for solving the above-described problem, a configuration is adopted in the present embodiment where the optical paths from the light sources to the sample substrate are made different by using mirrors 6a to 6c and 120a to 120c and condenser lenses 7a to 7c as illustrated in FIG. 11. The feature of the prism unit 18 is that the incidence plane or the exit plane serves as the exit plane or the incidence plane, respectively. According to the above-described configuration, the fine adjustment of the position and the size of the illumination area is performed by using microscopic-movement mechanisms of the positions and the tilts of the condenser lenses 7a to 7c so that the operability is improved. The mode of the present embodiment may be integrated into the first and second embodiments. In the first embodiment, however, it is desirable to form the bottom face of the prism unit into an isosceles triangle of $\alpha=\beta$.

Embodiment 4

Figure 12:
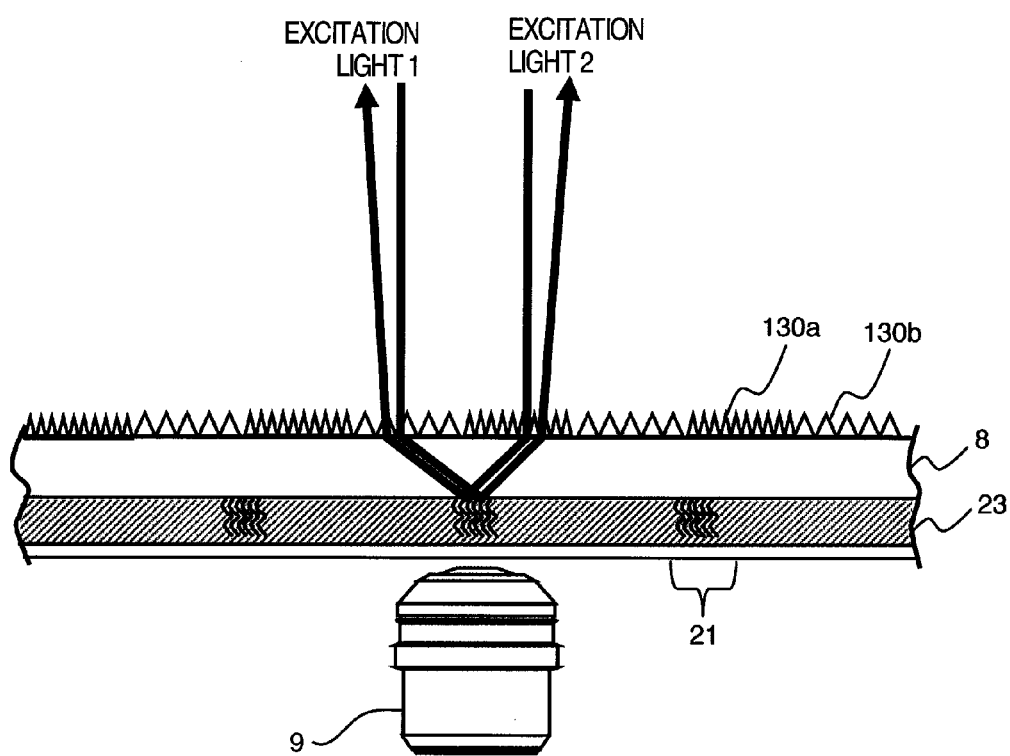
FIG. 12 illustrates a cross-sectional view including the excitation light path in the sample substrate in a fourth embodiment.

In the present embodiment, a configuration is shown which brings about the effect of preventing the illumination-position shift caused by scanning and the effect of reducing material cost of the prism units 18 as is the case with the second embodiment. FIG. 12 is an enlarged view around the sample substrate. It is characterized that there are provided on the sample substrate 8, diffraction-grating units 130a and 130b, whose lattice periods corresponding to the excitation wavelengths are different from each other. The other configurations are the same as the ones illustrated in FIG. 1 or FIG. 11. The lattice periods d of the diffraction-grating units are set such that $$\theta_p = \sin^{-1}(n\lambda/d) \quad \text{(Equation 6)}$$

where $\theta_p$ denotes the diffraction angles and (Equation 1) where $n_p$ denotes the refractive indexes of the diffraction-grating units are satisfied. Here, n denotes the diffraction order other than 0th order (an integer other than 0) and λ denotes the wavelengths of the excitation lights. While any diffraction order can be used for excitation, the diffraction-grating units are designed by setting n=+1 because the 1st-order diffraction efficiency is high in general. In particular, in the present embodiment, $\theta_p$ is so designed as to become the blazed angle by using the blazed diffraction gratings; other diffraction gratings such as holographic diffraction gratings and laminar-type diffraction gratings may also be used. The incidence excitation lights are totally-reflected on the interface between the sample solution 23 and the sample substrate 8 and, then, can exit from the diffraction-grating unit 130a or 130b.

Figure 13:
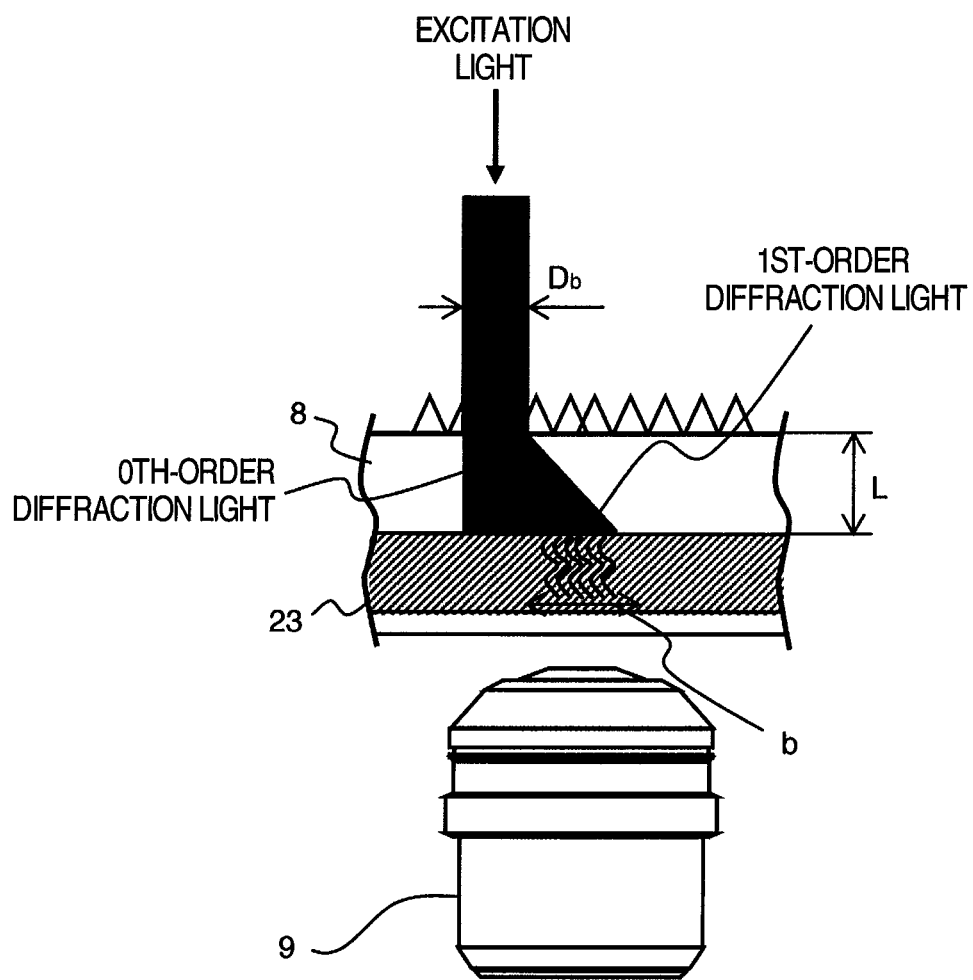
FIG. 13 illustrates an explanatory diagram when a 0th-order diffraction light and a 1st-order diffraction light are overlapped with each other in the fourth embodiment.

Also, as illustrated in FIG. 13, when the thickness L of the sample substrate 8 is small with respect to the beam diameter of the excitation light, the 0th-order diffraction light enters the observation field-of-view and a problem of intensified background light rises. Accordingly, the thickness of the sample substrate is required to be designed such that the following (Equation 7) is satisfied.

$$L \times \tan\theta_p > D_b/2 + b/2 \quad \text{(Equation 7)}$$

Here, $D_b$ is the beam diameter of the excitation light and b is the size of field-of-view in the diffraction direction (the X-axis direction in the present embodiment).

In the present embodiment, since the 1st-order diffraction angles differ significantly between the wavelengths of the light sources 1b and 1c used for the fluorescence measurement, diffraction-grating units which are optimized respectively for each wavelength are provided and excitation lights enter from the opposite directions. When the wavelengths of the two light sources are close to each other or a single diffraction grating can be used by using a single light source, a fabrication cost can be further suppressed. In the case of the single diffraction grating, the diffraction-grating unit may be provided on the entire surface of the sample substrate 8. While the formation of the diffraction-grating units is carried out by cutting the quarts sample substrate 8, it may also be carried out by attaching commercially-available diffraction gratings on the sample substrate 8 via the adhesive layer or by transferring a material other than quarts such as a resin from a master lattice. The characteristic advantages of the present embodiment are a capability of reducing the material compared with the case where the prisms are used since the size of the diffraction-grating units 130a and 130b can be suppressed down to a few µm or less and an additional capability of simplifying the optical-axis adjustment since the excitation lights can enter perpendicular to the sample substrate.

Embodiment 5

Figure 14:
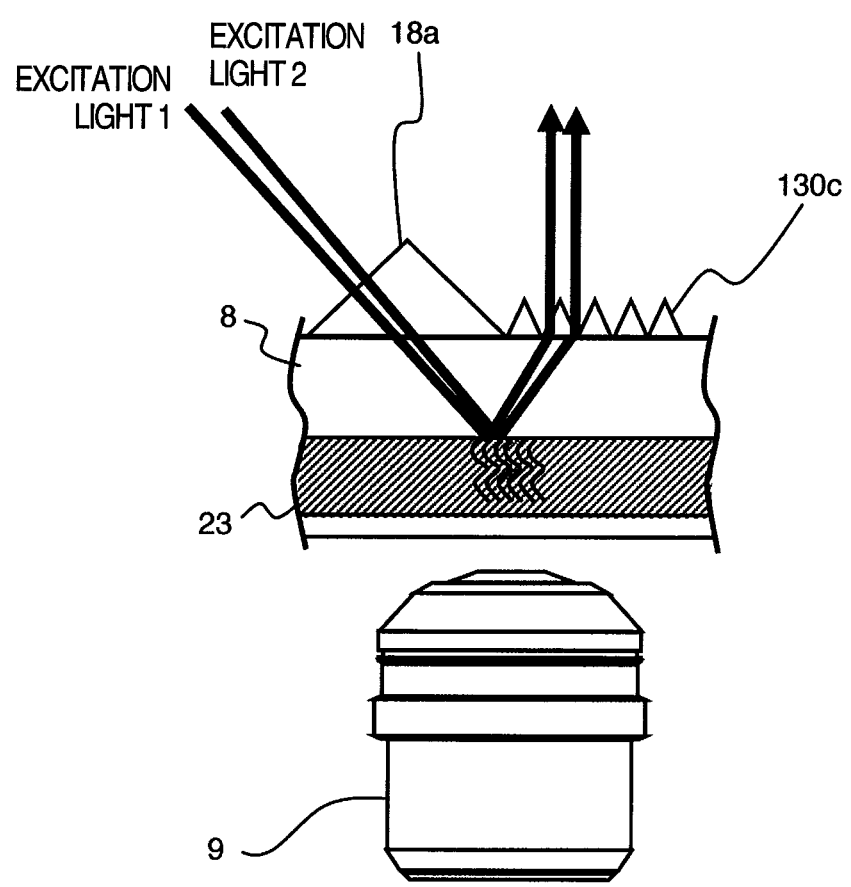
FIG. 14 illustrates a cross-sectional view including the excitation light path in the sample substrate in a fifth embodiment.
Figure 15:
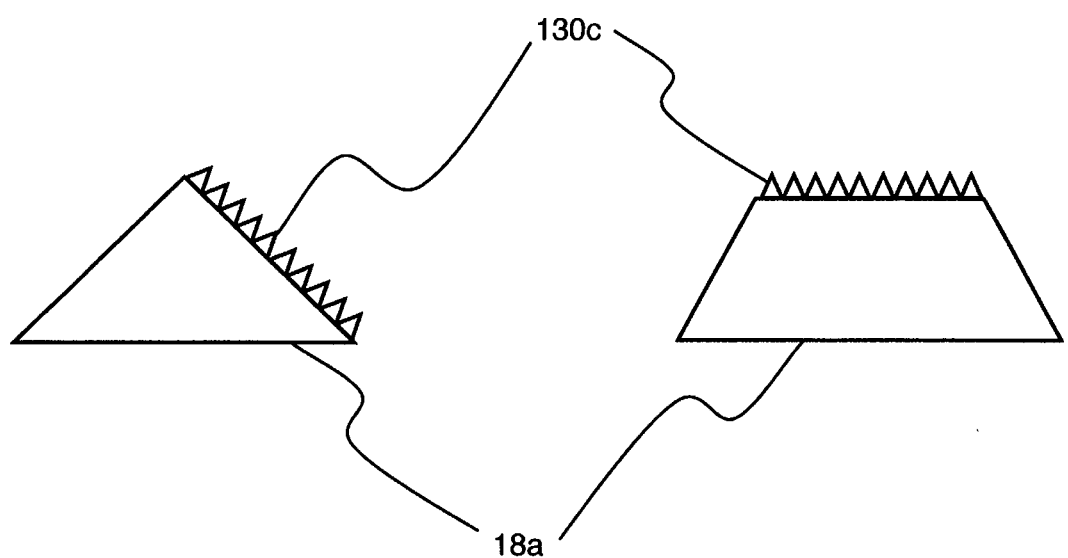
FIG. 15 illustrates forms of variations of the prism unit in the fifth embodiment.

The feature of the present embodiment is to use a prism unit 18a for the incidence plane of the excitation lights and a diffraction-grating unit 130c for the exit plane as illustrated in FIG. 14. The other configurations are the same as the ones illustrated in FIG. 1. In the case where the diffraction-grating units are provided for the incidence planes like the fourth embodiment, the diffraction angles are different from each other and it may be difficult to make the excitation lights of the plurality of wavelengths enter one and the same diffraction-grating unit. In the fourth embodiment, it is solved by providing the diffraction gratings which correspond to the two types of excitation lights as illustrated in FIG. 12. Three types or more of excitation lights, however, may become necessary depending on a combination of the fluorophores used for fluorescence observation and it may be difficult to implement a configuration where diffraction gratings corresponding respectively are integrated. Then, the use of the prism unit 18a for the incidence plane makes it possible to solve the above-described problem. On the other hand, by using the diffraction-grating unit 130c for the exit plane the material cost can be reduced compared with the second embodiment. Incidentally, a configuration may be used where a diffraction-grating unit 130c is provided on the exit plane of the prism units 18a as illustrated in FIG. 15. The present embodiment is also applicable to the case where the plurality of sample areas 21 share one prism unit in the X-axis direction like the first embodiment and the case where the prism-unit spacing and the sample-area spacing are made substantially equal to each other like the second embodiment.

Industrial Applicability

The present invention is applicable to apparatuses such as a DNA sequencer utilizing elongation reactions and a DNA micro-array chip analyzer of the total-reflection fluorescence scheme.

REFERENCE SIGNS LIST

1a, 1b, 1c: excitation lights
2a, 2b, 2c: shutters
3a, 3b, 3c; excitation filters
4a, 4b, 4c: λ/4 plates
5a, 5b: dichroic minors, 5c: minor
6, 6a, 6b, 6c, 120a, 120b, 120c: mirrors
7, 7a, 7b, 7c: condenser lens
8: sample substrate
9: objective lens
10: objective-lens driving unit
11a, 11b: light-emission filters
12: dispersion prism
14: image sensor
15: control unit
17: sample stage
18, 18a: prism units
19a: flow-in channel, 19b: flow-out channel,
21: sample areas
22: adhesive layer
23: sample solution
31: prism-unit incidence plane
32: prism-unit exit plane
41: illumination area
61: flow channel
62: solution-conveying unit
63: solution-storing unit
64a: sample reservoir, 64b: buffer reservoir, 64c: reaction-solution reservoir
65: waste-solution tank
71t, 71a, 71c, 71g: fluorescently-labeled nucleotides
72: double-stranded complex
73: metal structures
81: protecting group
101: sample-supporting member
102: sample-driving unit
130a, 130b, 130c: diffraction-grating units

The invention claimed is:

1. A fluorescence detector, comprising:
a light source;
a substrate which comprises:
   a first surface on an outer side of which a plurality of biosamples are arranged; and
   a second surface at which light from the light source enters, from which light totally reflected on an inner side of the first surface exits, and on an outer side of which a plurality of prisms are arranged with a prescribed period in a prescribed direction corresponding to areas where the plurality of biosamples are arranged;
a detector deployed adjacent to the outer side of the first surface of the substrate to detect light emitted from the biosamples excited by an evanescent field generated on the outer side of the first surface by the total reflection;
a driving unit which moves the substrate by the prescribed period of arrangement of the plurality of prisms so that a second biosample of the plurality of biosamples is measured after a first biosample of the plurality of biosamples is measured,
wherein the plurality of prisms are arranged in contact with each other on the second surface so that the light from the light source entering a first prism of the plurality of prisms is separated from a second prism of the plurality of prisms adjacent to the first prism,
wherein the areas the light from the light source irradiates are arranged on the substrate with the prescribed period in the prescribed direction.

2. The fluorescence detector according to claim 1, wherein the light emitted from the light source enters the plurality of prisms perpendicularly.

3. The fluorescence detector according to claim 1, wherein the plurality of prisms each corresponds to an area where one of the plurality of biosamples is deployed, and
the plurality of biosamples are arranged in the prescribed direction at a period equal to the prescribed period of the plurality of prisms.

4. The fluorescence detector according to claim 1, wherein the light source includes a first light source and a second light source, and
a plane which light from the light source enters the plurality of prisms and a plane which light from the light source exits the plurality of prisms are different for the first light source and the second light source.

5. The fluorescence detector according to claim 4, wherein two base angles formed by each of the plurality of prisms and the substrate are equal in magnitude.

* * * * *